United States Patent
Dieterle et al.

(10) Patent No.: US 7,019,176 B2
(45) Date of Patent: Mar. 28, 2006

(54) HETEROGENEOUSLY CATALYZED PARTIAL GAS PHASE OXIDATION OF PROPENE TO ACROLEIN

(75) Inventors: Martin Dieterle, Mannheim (DE); Jochen Petzoldt, Mannheim (DE); Klaus Joachim Mueller-Engel, Stutensee (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/784,778

(22) Filed: Feb. 24, 2004

(65) Prior Publication Data

US 2004/0225158 A1 Nov. 11, 2004

Related U.S. Application Data

(60) Provisional application No. 60/476,162, filed on Jun. 6, 2003.

(30) Foreign Application Priority Data

Mar. 25, 2003 (DE) .................. 103 13 212

(51) Int. Cl.
*C07C 45/35* (2006.01)

(52) U.S. Cl. ...................... 568/476; 568/479
(58) Field of Classification Search ............. 568/476, 568/479
See application file for complete search history.

(56) References Cited

U.S. PATENT DOCUMENTS

| | | | | |
|---|---|---|---|---|
| 4,438,217 A | * | 3/1984 | Takata et al. | 502/205 |
| 6,395,936 B1 | * | 5/2002 | Arnold et al. | 568/476 |
| 2004/0192963 A1 | | 9/2004 | Dieterle et al. | |
| 2004/0192964 A1 | | 9/2004 | Petzoldt et al. | |
| 2004/0192965 A1 | | 9/2004 | Petzoldt et al. | |
| 2004/0225158 A1 | | 11/2004 | Dieterle et al. | |
| 2004/0242926 A1 | | 12/2004 | Dieterle et al. | |

FOREIGN PATENT DOCUMENTS

| | | |
|---|---|---|
| DE | 199 10 506 A1 | 9/2000 |
| DE | 199 27 624 A1 | 12/2000 |
| DE | 199 48 241 A1 | 4/2001 |
| DE | 199 48 248 A1 | 4/2001 |
| DE | 199 48 523 A1 | 4/2001 |
| EP | 1 106 598 A2 | 6/2001 |
| EP | 1 159 244 | 12/2001 |
| WO | WO 00/53556 | 9/2000 |
| WO | WO 01/36364 | 5/2001 |

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

In a process for heterogeneously catalyzed partial gas phase oxidation of propene to acrolein, the starting reaction gas mixture is oxidized at a propene loading of <160 l (STP) of propene/l of fixed catalyst bed·h over a fixed catalyst bed which is accommodated in two successive reaction zones A, B, the highest temperature of the reaction gas mixture within reaction zone A being above the temperature of the reaction gas mixture within reaction zone B.

20 Claims, No Drawings

HETEROGENEOUSLY CATALYZED PARTIAL GAS PHASE OXIDATION OF PROPENE TO ACROLEIN

The present invention relates to a process for partially oxidizing propene to acrolein in the gas phase under heterogeneous catalysis by conducting a starting reaction gas mixture comprising propene, molecular oxygen and at least one inert gas, and containing the molecular oxygen and the propene in a molar $O_2:C_3H_6$ ratio of $\geq 1$, in one reaction stage over a fixed catalyst bed which is arranged in two spatially successive reaction zones A, B, the temperature of reaction zone A being a temperature in the range from 290 to 380° C. and the temperature of reaction zone B likewise being a temperature in the range from 290 to 380° C., and whose active composition is at least one multimetal oxide comprising the elements Mo, Fe and Bi, in such a way that reaction zone A extends up to a conversion of propene of from 40 to 80 mol % and, on single pass of the starting reaction gas mixture through the entire fixed catalyst bed, the propene conversion is $\geq 90$ mol % and the selectivity of acrolein formation, based on converted propene, is $\geq 90$ mol %, the chronological sequence in which the starting reaction gas mixture flows through the reaction zones corresponding to the alphabetic sequence of the reaction zones.

The abovementioned process of catalytic gas phase oxidation of propene to acrolein is generally known (cf., for example, DE-A 19910506) and is important in particular as the first oxidation stage in the preparation of acrylic acid by two-stage catalytic gas phase oxidation starting from propene. Acrylic acid is an important monomer which finds use as such or in the form of its alkyl ester for obtaining polymers suitable, for example, as adhesives. Acrolein is an important intermediate.

In addition to molecular oxygen and the reactants, the starting reaction gas mixture comprises inert gas in order to keep the reaction gas outside the explosion limit, among other reasons.

One objective of such a heterogeneously catalyzed partial gas phase oxidation of propene to acrolein is to achieve a very high yield $Y^{AC}$ of acrolein (main product) (this is the number of moles of propene converted to acrolein, based on the number of moles of propene used) on single pass of the reaction gas mixture through the reaction stage under otherwise predefined boundary conditions.

A further object of such a heterogeneously catalyzed partial gas phase oxidation of propene to acrolein is to achieve a very high space-time yield ($STY^{AC}$) of acrolein (in a continuous procedure, this is the total amount of acrolein obtained per hour and unit of volume of the fixed catalyst bed used in liters).

At a constant given yield $Y^{AC}$, the greater the hourly space velocity of propene on the fixed catalyst bed of the reaction stage (this refers to the amount of propene in liters at STP (=l (STP); the volume in liters which would be taken up by the appropriate amount of propene under standard conditions, i.e. at 25° C. and 1 bar) which is conducted as a constituent of the starting reaction gas mixture through 1 liter of fixed catalyst bed per hour), the higher the space-time yield.

The teachings of the documents WO 01/36364, DE-A 19927624, DE-A 19948248, DE-A 19948523, DE-A 19948241 and DE-A 19910506 are therefore directed toward significantly increasing the hourly space velocity of propene on the fixed catalyst bed of the reaction stage at substantially constant $Y^{AC}$. This is achieved substantially by arranging the fixed catalyst bed in the reaction stage in two spatially successive reaction zones (reaction zones). The hourly space velocity of propene on the fixed catalyst bed selected is $\geq 160$ l (STP)/l of fixed catalyst bed·h and the temperature of the second (in the flow direction of the reaction gas mixture) reaction zone in each case has to be at least 5° C. above the temperature of the first reaction zone.

In a similar manner, EP-A 1106598 also teaches a process of the high loading method for the heterogeneously catalyzed partial gas phase oxidation of propene to acrolein, in which the fixed catalyst bed of the reaction stage is arranged in a plurality of reaction zones. According to the teaching of EP-A 1106598, the temperature difference of a subsequent reaction zone in the flow direction of the reaction gas mixture can be either more or less than 5° C. above the temperature of the preceding reaction zone, and EP-A 1106598 leaves completely open the question of under which conditions a larger and under which conditions a smaller temperature difference should be applied.

EP-A 1106598 also leaves completely open the definition of the temperature of a reaction or reaction zone.

In contrast, the remaining documents of the cited prior art define the temperature of a reaction zone as the temperature in the fixed catalyst bed disposed in the reaction zone when performing the process in the absence of a chemical reaction. When this temperature is not constant within the reaction zone, the term temperature of a reaction zone then refers to the (numerical) mean of the temperature of the fixed catalyst bed along the reaction zone. It is essential that the individual reaction zones are heated substantially independently, so that a reaction zone always corresponds to a reaction zone. The aforementioned definition of the temperature of a reaction zone also applies in this document.

Since the heterogeneously catalyzed partial gas phase oxidation of propene to acrolein is a markedly exothermic reaction, the temperature of the reaction gas mixture on reactive pass through the fixed catalyst bed is generally different to the temperature of a reaction zone. It is normally above the temperature of the reaction zone and, within a reaction zone, generally passes through a maximum (heating point maximum) or falls starting from a maximum value.

However, a disadvantage of the teachings of the prior art is that they are exclusively directed toward operating a multizone arrangement under a high propene loading. This is disadvantageous in that such a procedure is inevitably accompanied by a high $STY^{AC}$. This assumes a corresponding market demand for acrolein and/or acrylic acid. When the latter is not present (for example temporarily), the multizone arrangement necessarily has to be operated at lower propene loadings, and the target quantity to be pursued which then also comes to the forefront is a very high selectivity of acrolein formation, based on converted propene ($S^{AC}$). On single pass through the multizone arrangement, this is the molar amount of acrolein formed, based on the number of moles of propene converted.

It is an object of the present invention to provide a process for partially oxidizing propene to acrolein in the gas phase under heterogeneous catalysis in a multizone arrangement, in which acrolein is formed at very high selectivity at propene loadings of <160 l (STP)/l·h.

We have found that this object is achieved by a process for partially oxidizing propene to acrolein in the gas phase under heterogeneous catalysis by conducting a starting reaction gas mixture comprising propene, molecular oxygen and at least one inert gas, and containing the molecular oxygen and the propene in a molar $O_2:C_3H_6$ ratio of $\geq 1$, in one reaction stage over a fixed catalyst bed which is arranged in two spatially successive reaction zones A, B, the temperature of reaction zone A being a temperature in the range from 290 to 380° C. and the temperature of reaction zone B likewise being a temperature in the range from 290 to 380° C., and whose active composition is at least one multimetal oxide comprising the elements Mo, Fe and Bi, in such a way that reaction zone A extends up to a conversion of propene of from 40 to 80 mol % and, on single pass of the starting reaction gas mixture through the entire fixed catalyst bed, the propene conversion is ≧90 mol % and the selectivity of acrolein formation, based on converted propene, is ≧90 mol %, the chronological sequence in which the starting reaction gas mixture flows through the reaction zones corresponding to the alphabetic sequence of the reaction zones, wherein a) the hourly space velocity of the propene contained in the starting reaction gas mixture on the fixed catalyst bed is <160 l (STP) of propene/l of fixed catalyst bed·h and ≧90 l (STP) of propene/l of fixed catalyst bed·h, b) the volume-specific activity of the fixed catalyst bed is either constant or increases at least once in the flow direction of the reaction gas mixture over the fixed catalyst bed, and c) the difference $T^{maxA}-T^{maxB}$, formed from the highest temperature $T^{maxA}$ which the reaction gas mixture has within reaction zone A and the highest temperature $T^{maxB}$ which the reaction gas mixture has within reaction zone B, is ≧0° C.

The volume-specific activity of the fixed catalyst bed preferably increases at least once in the flow direction.

In general, the difference $T^{maxA}-T^{maxB}$ in the process according to the invention will not be more than 80° C. According to the invention, $T^{maxA}-T^{maxB}$ is preferably ≧3° C. and ≦70° C. Very particularly preferably, $T^{maxA}-T^{maxB}$ in the process according to the invention is ≧20° C. and ≦60° C.

The process according to the invention proves advantageous, for example, when the hourly space velocity of the propene contained in the starting reaction gas mixture on the fixed catalyst bed is ≧90 l (STP) of propene/l·h and ≦155 l (STP) of propene/l·h, or ≧100 l (STP) of propene/l·h and ≦150 l (STP) of propene/l·h, or ≧110 l (STP) of propene/l·h and ≦145 l (STP) of propene/l·h, or ≧120 l (STP) of propene/l·h and ≦140 l (STP) of propene/l·h, or ≧125 l (STP) of propene/l·h and ≦135 l (STP) of propene/l·h.

It will be appreciated that the process according to the invention can also be applied when the hourly space velocity of the acrolein contained in the reaction gas mixture on the fixed catalyst bed is <90 l (STP) of acrolein/l·h. However, the operation of a multizone arrangement at such low reactant loadings would hardly be economic.

When performing the process according to the invention, the differences $T^{maxA}-T^{maxB}$ required according to the invention are normally attained when, on the one hand, both the temperature of reaction zone A and the temperature of reaction zone B are in the range from 290 to 380° C. and, on the other hand, the difference between the temperature of reaction zone B ($T_B$) and the temperature of reaction zone A ($T_A$), i.e. $T_B-T_A$, is ≦0° C. and ≧-10° C., or ≦0° C. and ≧-5° C., or frequently ≦0° C. and ≧-3° C.

In other words, in contrast to the teaching of the prior art for high loadings, the temperature of the subsequent zone in the process according to the invention will normally be lower than the temperature of the preceding reaction zone.

The abovementioned statement relating to the temperature differences $T_B-T_A$ also applies when the temperature of reaction zone A is in the preferred range from 305 to 365° C. or in the particularly preferred range from 310 to 340° C.

The working pressure in the process according to the invention can either be below atmospheric pressure (for example down to 0.5 bar) or above atmospheric pressure. Typically, the working pressure will be at values of from 1 to 5 bar, frequently from 1 to 3 bar. Normally, the reaction pressure will not exceed 100 bar.

According to the invention, reaction zone A preferably extends up to a conversion of propene of from 50 to 70 mol %, or from 60 to 70 mol %.

In general, the propene conversion based on single pass in the process according to the invention can be ≧92 mol %, or ≧94 mol %, or ≧96 mol %. The selectivity of acrolein formation will regularly be ≧92 mol %, or ≧94 mol %, frequently ≧95 mol % or ≧96 mol %, or ≧97 mol %.

According to the invention, the molar $O_2$:propene ratio in the starting reaction gas mixture has to be ≧1. Frequently, it is at values of >1. Typically, this ratio will be at values of ≦3. According to the invention, the molar $O_2$:propene ratio in the starting reaction gas mixture will frequently be from 1 to 2, or from 1 to 1.5.

A useful source for the molecular oxygen required is either air or air enriched with molecular nitrogen.

Useful catalysts for the fixed catalyst bed of the process according to the invention include all of those catalysts whose active composition is at least one multimetal oxide comprising Mo, Bi and Fe.

These are in particular the multimetal oxide active compositions of the general formula I of DE-A 19955176, the multimetal oxide active compositions of the general formula I of DE-A 19948523, the multimetal oxide active compositions of the general formulae I, II and III of DE-A 10101695, the multimetal oxide active compositions of the general formulae I, II and III of DE-A 19948248 and the multimetal oxide active compositions of the general formulae I, II and III of DE-A 19955168 and also the multimetal oxide active compositions specified in EP-A 700714.

Also suitable for the fixed catalyst bed are the multimetal oxide catalysts comprising Mo, Bi and Fe which are disclosed in the documents DE-A 10046957, DE-A 10063162, DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the general formula II), JP-A 91/294239, EP-A 293224 and EP-A 700714. This applies in particular for the exemplary embodiments in these documents, and among these particular preference is given to those of EP-A 15565, EP-A 575897, DE-A 19746210 and DE-A 19855913. Particular emphasis is given in this context to a catalyst according to example 1 c from EP-A 15565 and also to a catalyst to be prepared in a corresponding manner but having the active composition $Mo_{12}Ni_{6.5}Zn_2Fe_2Bi_1P_{0.0065}K_{0.06}O_x$. 10 $SiO_2$. Emphasis is also given to the example having the serial number 3 from DE-A 19855913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm or 5 mm×2 mm×2 mm (each external diameter×height×internal diameter) and also to the unsupported multimetal oxide II catalyst according to example 1 of DE-A 19746210. Mention should also be made of the multimetal oxide catalysts of U.S. Pat. No. 4,438,217. The latter is true in particular when these have a hollow cylinder geometry of the dimensions 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Likewise suitable are the multimetal oxide catalysts and geometries of DE-A 10101695 or WO 02/062737.

Also suitable are example 1 of DE-A 10046957 (stoichiometry: [Bi$_2$W$_2$O$_9$×2WO$_3$]$_{0.5}$·[Mo$_{12}$Co$_{5.6}$Fe$_{2.94}$Si$_{1.59}$K$_{0.08}$O$_x$]$_1$) as an unsupported hollow cylinder (ring) catalyst of geometry 5 mm×3 mm×2 mm or 5 mm×2 mm×2 mm (each external diameter×length×internal diameter), and also the coated catalysts 1, 2 and 3 of DE-A 10063162 (stoichiometry: Mo$_{12}$Bi$_{1.0}$Fe$_3$Co$_7$Si$_{1.6}$K$_{0.08}$), except as annular coated catalysts of appropriate coating thickness and applied to support rings of geometry 5 mm×3 mm×1.5 mm or 7 mm×3 mm×1.5 mm (each external diameter×length×internal diameter).

A multiplicity of the multimetal oxide active compositions suitable for the catalysts of the fixed catalyst bed can be encompassed by the general formula I

$$Mo_{12}Bi_aFe_bX^1_cX^2_dX^3_eX^4_fO_n \qquad (I)$$

where the variables are defined as follows:
X$^1$=nickel and/or cobalt,
X$^2$=thallium, an alkali metal and/or an alkaline earth metal,
X$^3$=zinc, phosphorus, arsenic, boron, antimony, tin, cerium, lead and/or tungsten,
X$^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in I other than oxygen.

They are obtainable in a manner known per se (see, for example, DE-A 4023239) and are customarily shaped undiluted to give spheres, rings or cylinders or else used in the form of coated catalysts, i.e. preshaped inert support bodies coated with the active composition. It will be appreciated that they may also be used as catalysts in powder form.

In principle, active compositions of the general formula I can be prepared in a simple manner by obtaining a very intimate, preferably finely divided dry mixture corresponding to their stoichiometry from suitable sources of their elemental constituents and calcining it at temperatures of from 350 to 650° C. The calcination may be effected either under inert gas or under an oxygen atmosphere, for example air (mixture of inert gas and oxygen) and also under a reducing atmosphere (for example mixture of inert gas, NH$_3$, CO and/or H$_2$). The calcination time can be from a few minutes to a few hours and typically decreases with temperature. Useful sources for the elemental constituents of the multimetal oxide active compositions I are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as NH$_4$OH, (NH$_4$)$_2$CO$_3$, NH$_4$NO$_3$, NH$_4$CHO$_2$, CH$_3$COOH, NH$_4$CH$_3$CO$_2$ and/or ammonium oxalate, which decompose and/or can be decomposed on later calcining at the latest to release compounds in gaseous form can be additionally incorporated into the intimate dry mixture).

The starting compounds for preparing the multimetal oxide active compositions I can be intimately mixed in dry or in wet form. When they are mixed in dry form, the starting compounds are advantageously used as finely divided powders and subjected to calcination after mixing and optional compacting. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

Typically, the multimetal oxide active compositions of the general formula I are used in the fixed catalyst bed not in powder form, but rather shaped into certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of unsupported catalyst geometries include solid cylinders or hollow cylinders having an external diameter and a length of from 2 to 10 mm. In the case of the hollow cylinder, a wall thickness of from 1 to 3 mm is advantageous. It will be appreciated that the unsupported catalyst can also have spherical geometry, and the spherical diameter can be from 2 to 10 mm.

A particularly advantageous hollow cylinder geometry is 5 mm×3 mm×2 mm (external diameter×length×internal diameter), in particular in the case of unsupported catalysts.

It will be appreciated that the pulverulent active composition or its pulverulent precursor composition which is yet to be calcined and/or partially calcined can be shaped by applying to preshaped inert catalyst supports. The coating of the support bodies to produce the coated catalysts is generally performed in a suitable rotatable vessel, as disclosed, for example, by DE-A 2909671, EP-A 293859 or EP-A 714700. To coat the support bodies, the powder composition to be applied is advantageously moistened and dried again after application, for example by means of hot air. The coating thickness of the powder composition applied to the support body is advantageously selected within the range from 10 to 1 000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave inertly with regard to the target reaction on which the process according to the invention in the first reaction stage is based. The support bodies may have a regular or irregular shape, although preference is given to regularly shaped support bodies having a distinct surface roughness, for example spheres or hollow cylinders. It is suitable to use substantially nonporous, surface-roughened spherical supports made of steatite (e.g. Steatite C220 from CeramTec) whose diameter is from 1 to 8 mm, preferably from 4 to 5 mm. However, suitable support bodies also include cylinders whose length is from 2 to 10 mm and whose external diameter is from 4 to 10 mm. In the case of rings suitable as support bodies according to the invention, the wall thickness is also typically from 1 to 4 mm. According to the invention, annular support bodies to be used preferably have a length of from 2 to 6 mm, an external diameter of from 4 to 8 mm and a wall thickness of from 1 to 2 mm. Suitable as support bodies according to the invention are in particular rings of geometry 7 mm×3 mm×4 mm (external diameter×length× internal diameter). It will be appreciated that the fineness of the catalytically active oxide compositions to be applied to the surface of the support body will be adapted to the desired coating thickness (cf. EP-A 714 700).

Suitable multimetal oxide active compositions for the catalysts of the first reaction stage are also compositions of the general formula II

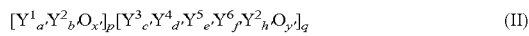

where the variables are defined as follows:
$Y^1$=only bismuth or bismuth and at least one of the elements, tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from 0 to 20,
f'=from 0 to 6,
g'=from 0 to 15,
h'=from 8 to 16,
x',y'=numbers which are determined by the valency and frequency of the elements in II other than oxygen and
p,q=numbers whose p/q ratio is from 0.1 to 10, comprising three-dimensional regions of the chemical composition $Y^1_a Y^2_b O_{x'}$ which are delimited from their local environment as a consequence of their different chemical composition from their local environment, and whose maximum diameter (longest line through the center of the region and connecting two points on the surface (interface) of the region) is from 1 nm to 100 μm, frequently from 10 nm to 500 nm or from 1 μm to 50 or 25 μm.

Particularly advantageous multimetal oxide compositions II according to the invention are those in which $Y^1$ is only bismuth.

Among these, preference is given in turn to those of the general formula III

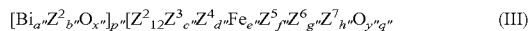

where the variables are defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably from 0.1 to 3,
f"=from 0 to 5,
g"=from 0 to 10,
h"=from 0 to 1,
x",y"=numbers which are determined by the valency and frequency of the elements in III other than oxygen,
p",q"=numbers whose p"/q" ratio is from 0.1 to 5, preferably from 0.5 to 2, and particular preference is given to those compositions III in which $Z^2_{b"}$=(tungsten)$_{b"}$ and $Z^2_{12}$=(molybdenum)$_{12}$.

It is also advantageous when at least 25 mol % (preferably at least 50 mol % and more preferably at least 100 mol %) of the total proportion of $[Y^1_a Y^2_b O_{x'}]_p$ ($[Bi_{a"} Z^2_{b"} O_{x"}]_{p"}$) of the multimetal oxide compositions II (multimetal oxide compositions III) suitable according to the invention in the multimetal oxide compositions II (multimetal oxide compositions III) suitable according to the invention are in the form of three-dimensional regions of the chemical composition $Y^1_a Y^2_b O_{x'} [Bi_{a"} Z^2_{b"} O_{x"}]$ which are delimited from their local environments as a consequence of their different chemical composition from their local environment, and whose maximum diameter is in the range from 1 nm to 100 μm.

With regard to the shaping, the statements made for the multimetal oxide I catalysts apply to the multimetal oxide II catalysts.

The preparation of multimetal oxide II active compositions is described, for example, in EP-A 575897 and also in DE-A 19855913.

To prepare the fixed catalyst bed in the process according to the invention, it is possible to use only the appropriate shaped catalyst bodies having multimetaloxide active composition or else substantially homogeneous mixtures of shaped catalyst bodies having multimetal oxide active composition and shaped bodies (shaped diluent bodies) having no multimetal oxide active composition and behaving substantially inertly with regard to the heterogeneously catalyzed partial gas phase oxidation. Useful materials for such inert shaped bodies are in principle all of those which are suitable as support material for coated catalysts suitable according to the invention. Examples of such materials include porous or nonporous aluminum oxides, silicon dioxide, thorium dioxide, zirconium dioxide, silicon carbide, silicates such as magnesium silicate or aluminum silicate or the steatite already mentioned above (e.g. Steatite C-220 from CeramTec).

The geometry of such inert shaped diluent bodies may in principle be as desired. In other words, they may, for example, be spheres, polygons, solid cylinders or else rings. According to the invention, the inert diluent bodies selected will preferably be those whose geometry corresponds to that of the shaped catalyst bodies to be diluted by them.

According to the invention, it is advantageous when the chemical composition of the active composition used does not change over the fixed catalyst bed. In other words, although the active composition used for an individual shaped catalyst body may be a mixture of different multimetal oxides comprising the elements Mo, Fe and Bi, the same mixture then has to be used for all shaped catalyst bodies of the fixed catalyst bed.

In this case, the volume-specific (i.e. normalized to the unit of volume) activity can be reduced in a simple manner, for example, by homogeneously diluting a basic amount of shaped catalyst bodies prepared in a uniform manner with shaped diluent bodies. The higher the proportion of shaped diluent bodies selected, the less active composition and catalyst activity are present in a certain volume of the bed.

A volume-specific activity increasing at least once in the flow direction of the reaction gas mixture over the fixed catalyst bed can therefore be achieved in a simple manner for the process according to the invention, for example, by beginning the bed with a high proportion of inert shaped diluent bodies based on one type of shaped catalyst bodies, and then reducing this proportion of shaped diluent bodies in the flow direction either continuously or, at least once or more than once, abruptly (for example step-wise). When the proportion of shaped diluent bodies is left constant or no shaped diluent bodies at all are used in the fixed catalyst bed, this then results in a constant volume-specific activity in the flow direction of the reaction gas mixture over the fixed catalyst bed. However, an increase in the volume-specific activity is also possible, for example, by increasing the thickness of the active composition layer applied to the support at constant geometry and active composition type of a coated shaped catalyst body, or, in a mixture of coated catalysts having the same geometry but different proportions by weight of active composition, increasing the proportion of shaped catalyst bodies having higher active composition content. Alternatively, the active compositions themselves can be diluted in the course of the active composition preparation by, for example, incorporating inert, diluting materials such as hard-fired silica into the dry mixture of starting compounds to be calcined. Different amounts of diluting material added automatically lead to different activities. The more diluting material is added, the lower the resulting activity will be. A similar effect can also be achieved, for example, by varying the mixing ratio in mixtures of unsupported catalysts and of coated catalysts (having identical active composition) in an appropriate manner. It will be appreciated that the variants described can also be used in combination.

It is of course also possible to use mixtures of catalysts having chemically different active compositions and, as a consequence of these different compositions, different activities for the fixed catalyst bed. These mixtures may in turn be diluted with inert diluent bodies.

Normally, the volume-specific activity in the process according to the invention will never decrease within the fixed catalyst bed in the flow direction of the reaction gas mixture.

Upstream and/or downstream of the fixed catalyst bed may be disposed beds consisting exclusively of inert material (for example only shaped diluent bodies) (in this document, they are not included for terminology purposes in the fixed catalyst bed, since they contain no shaped bodies which have multimetal oxide active composition). The shaped diluent bodies used for the inert bed can have the same geometry as the shaped catalyst bodies used in the fixed catalyst bed. However, the geometry of the shaped diluent bodies used for the inert bed may also be different to the above-mentioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having the diameter d=4–5 mm.

According to the invention, preference is given to the fixed catalyst bed in the process according to the invention being structured as follows in the flow direction of the reaction gas mixture.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the fixed bed catalyst bed 1, a homogeneous mixture of shaped catalyst bodies and shaped diluent bodies (both preferably having substantially the same geometry), in which the proportion by weight of the shaped diluent bodies (the densities of shaped catalyst bodies and of shaped diluent bodies generally differ only slightly) is normally from 5 to 40% by weight, or from 10 to 40% by weight, or from 20 to 40% by weight, or from 25 to 35% by weight. According to the invention, this first zone of the fixed catalyst bed is advantageously followed up to the end of the length of the fixed catalyst bed (i.e., for example, to a length of from 2.00 to 3.00 m, preferably from 2.50 to 3.00 m) either by a bed of shaped catalyst bodies diluted only to a slighter extent (than in the first zone), or, most preferably, an unaccompanied (undiluted) bed of the same shaped catalyst bodies which have also been used in the first zone. The aforesaid applies in particular when the shaped catalyst bodies used in the fixed catalyst bed are unsupported catalyst rings or coated catalyst rings (in particular those which are specified as preferred in this document). For the purposes of the abovementioned structuring, both the shaped catalyst bodies and the shaped diluent bodies in the process according to the invention advantageously have substantially the ring geometry 5 mm×3 mm×2 mm (external diameter×length×internal diameter).

In an advantageous manner from an application point of view, the reaction stage of the process according to the invention is carried out in a two-zone tube bundle reactor, as described, for example, in DE-A 19910508, 19948523, 19910506 and 19948241. A preferred variant of a two-zone tube bundle reactor which can be used in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903218 are also suitable for carrying out the first reaction stage of the process according to the invention.

In other words, in the simplest manner, the fixed catalyst bed to be used in accordance with the invention (possibly with downstream and/or upstream inert beds) is disposed in the metal tubes of a tube bundle reactor and two spatially separated heating media, generally salt melts, are conducted around the metal tubes. The tube section over which the particular salt bath extends represents a reaction zone in accordance with the invention. In other words, in the simplest manner, for example, a salt bath A flows around that section of the tubes (reaction zone A) in which propene is oxidatively converted (on single pass) until a conversion value in the range from 40 to 80 mol % is achieved, and a salt bath B flows around the section of the tubes (reaction zone B) in which the propene is subsequently oxidatively converted (on single pass) until a conversion value of at least 90 mol % is achieved (if required, the reaction zones A, B to be used in accordance with the invention can be followed by further reaction zones which are maintained at individual temperatures).

It is advantageous from an application point of view if the first reaction stage of the process according to the invention includes no further reaction zones. In other words, the salt bath B advantageously flows around the section of the tubes in which propene is subsequently oxidatively converted (on single pass) up to a conversion value of ≧90 mol %, or ≧92 mol %, or ≧94 mol % or more.

Typically, the beginning of the reaction zone B lies beyond the heating point maximum of reaction zone A.

According to the invention, both salt baths A, B can be conducted in cocurrent or in countercurrent through the space surrounding the reaction tubes relative to the flow direction of the reaction gas mixture flowing through the reaction tubes. It will be appreciated that, in accordance with the invention, cocurrent flow may be applied in reaction zone A and countercurrent flow in reaction zone B (or vice versa).

In all of the aforementioned cases, it will be appreciated that a transverse flow can be superimposed on the parallel flow of the salt melt relative to the reaction tubes taking place within the particular reaction zone, so that the individual reaction zone corresponds to a tube bundle reactor as described in EP-A 700714 or in EP-A 700893, which results overall in a meandering flow profile of the heat exchange medium in a longitudinal section through the catalyst tube bundle.

Advantageously, the starting reaction gas mixture 1 in the process according to the invention is fed to the fixed catalyst bed 1 preheated to the reaction temperature.

Typically, the catalyst tubes in the two-zone tube bundle reactors are manufactured from ferritic steel and typically have a wall thickness of from 1 to 3 mm. Their internal diameter is generally from 20 to 30 mm, frequently from 21 to 26 mm. Their length is advantageously from 2 to 4 m, preferably from 2.5 to 3.5 m. In each reaction zone, the fixed catalyst bed 1 occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5 000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (the catalyst tube pitch) is from 35 to 45 mm (cf., for example, EP-B 468290).

Useful heat exchange media for the two-zone method are also in particular fluid heating media. It is particularly advantageous to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-zone tube bundle reactors, the flow rate within the two heat exchange medium circuits required is selected in such a way that the temperature of the heat exchange medium rises from the entrance into the reaction zone to the exit from the reaction zone (as a result of the exothermicity of the reaction) by from 0 to 15° C. In other words, the aforementioned ΔT may be from 1 to 10° C., or from 2 to 8° C., or from 3 to 6° C., in accordance with the invention.

According to the invention, the entrance temperature of the heat exchange medium into reaction zone A is normally in the range from 290 to 380° C., preferably in the range from 305 to 365° C. and more preferably in the range from 310 to 340° C. or is 330° C. According to the invention, the entrance temperature of the heat exchange medium into reaction zone B is likewise normally in the range from 290 to 380° C., but at the same time normally from $\geq 0°$ C. to $\leq 10°$ C., or $\geq 0°$ C. and $\leq 5°$ C., or frequently $\geq 0°$ C. and $\leq 3°$ C., below the entrance temperature of the heat exchange medium entering reaction zone A.

It is pointed out once again at this juncture that, for an implementation of the reaction stage of the process according to the invention, it is possible to use in particular the two-zone tube bundle reactor type described in DE-B 2201528 which includes the possibility of removing a portion of the hotter heat exchange medium of reaction zone B to reaction zone A, in order to optionally heat a cold starting reaction gas mixture or a cold cycle gas. The tube bundle characteristics within an individual reaction zone may also be configured as described in EP-A 382098.

The acrolein can be removed from the product gas mixture leaving the reaction stage in a manner known per se and the remaining residual gas can be at least partly recycled as diluent gas into the propene partial oxidation in a manner known per se. However, it will advantageously be used for charging a subsequent heterogeneously catalyzed partial oxidation of the acrolein contained therein to acrylic acid. It will advantageously be cooled in a direct and/or indirect manner before entry into such a subsequent reaction stage in order to suppress subsequent full combustion of portions of the acrolein formed in the propene oxidation stage.

To this end, an aftercooler is customarily inserted between the two reaction stages. In the simplest case, this may be an indirect tube bundle heat exchanger. Subsequently, oxygen is supplemented in the form of air, in order to provide a superstoichiometric oxygen content advantageous for such an acrolein oxidation.

The propene content in the starting reaction gas mixture in the process according to the invention can, for example, be at values of from 4 to 15% by volume, frequently at from 5 to 12% by volume, or from 5 to 8% by volume (based in each case on the total volume).

Frequently, the process according to the invention will be carried out as a propene:oxygen:inert gases (including steam) volume ratio in the starting reaction gas mixture 1 of 1:(1.0 to 3.0):(5 to 25), preferably 1:(1.7 to 2.3):(10 to 15). least 20% of the volume of the inert gas will consist of molecular nitrogen. However, $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of the inert gas may consist of molecular nitrogen (in this document, inert diluent gases generally refer to those of which less than 5%, preferably less than 2%, is converted in single pass through the reaction stage; in addition to molecular nitrogen, these are, for example, gases such as propane, ethane, methane, pentane, butane, $CO_2$, CO, steam and/or noble gases). Of course up to 50 mol %, or up to 75 mol % and more of the inert diluent gas in the process according to the invention can consist of propane. Cycle gas, as remains after the removal of the acrolein and/or acrylic acid (for example in the case of a downstream second oxidation stage) from the product gas mixture, can also be a constituent of diluent gas.

The starting reaction gas mixtures which are advantageous according to the invention are, for example, those which are composed of

| | |
|---|---|
| from 6 to 15 (preferably from 7 to 11) % by volume | of propene, |
| from 4 to 20 (preferably from 6 to 12) % by volume | of water, |
| from $\geq 0$ to 10 (preferably from $\geq 0$ to 5) % by volume | of constituents other than propene, water, oxygen and nitrogen, | sufficient molecular oxygen that the molar ratio of molecular oxygen present to propene present is from 1.5 to 2.5 (preferably from 1.6 to 2.2), and the remainder up to 100% by volume of the total amount of molecular nitrogen, as recommended by DE-A 10302715.

It is emphasized at this juncture that the multimetal oxide compositions of DE-A 10261186 are also advantageous as active compositions for the fixed catalyst bed.

Designs of a two-zone tube bundle reactor for the first reaction stage which are advantageous in accordance with the invention can have the following construction (the detailed configuration of the construction can be as described in the utility model applications 202 19 277.6, 2002 19 278.4 and 202 19 279.2 or in the PCT applications PCT/EP02/14187, PCT/EP02/14188 or PCT/EP02/14189):

Catalyst Tubes:

material of the catalyst tubes: ferritic steel;

dimensions of the catalyst tubes: length, for example, 3 500 mm;

external diameter, for example, 30 mm wall thickness, for example, 2 mm;

number of catalyst tubes in the tube bundle: for example, 30 000, or 28 000, or 32 000, or 34 000; in addition up to 10 thermal tubes (as described in EP-A 873 783 and EP-A 12 70 065) which are charged in the same way as the catalyst tubes (in a spiral manner rotating from the very outside toward the inside), for example of the same length and wall thickness but having an external diameter of, for example, 33.4 mm and a centered thermowell of external diameter, for example, 8 mm and wall thickness of, for example, 1 mm;

reactor (same material as the catalyst tubes):

cylindrical vessel of internal diameter 6 000–8 000 mm;

reactor hoods plated with stainless steel of the type 1.4541; plating thickness: a few mm;

annularly arranged tube bundle, for example with free central space:

diameter of the free central space: for example, 1 000–2 500 mm (for example 1200 mm, or 1 400 mm, or 1 600 mm, or 1 800 mm, or 2 000 mm, or 2 200 mm, or 2 400 mm);

normally homogeneous catalyst tube distribution in the tube bundle (6 equidistant adjacent tubes per catalyst tube), arrangement in an equilateral triangle, catalyst tube pitch (separation of the central internal axes of immediately adjacent catalyst tubes): 35–45 mm, for example 36 mm, or 38 mm, or 40 mm, or 42 mm, or 44 mm;

the catalyst tubes are secured and sealed by their ends in catalyst tube plates (upper plate and lower plate each having a thickness, for example, of 100–200 mm) and open at their upper ends into a hood joined to the vessel which has an inlet for the starting reaction gas mixture; a separating plate of thickness 20–100 mm disposed, for example, at half the catalyst tube length, divides the reactor space symmetrically into two reaction zones (temperature zones) A (upper zone) and B (lower zone); each reaction zone is divided into 2 equidistant longitudinal sections by a deflecting plate;

the deflecting plate preferably has annular geometry; the catalyst tubes are advantageously secured and sealed at the separating plate; they are not secured and sealed at the deflecting plates, so that the transverse flow rate of the salt melt within one zone is very constant;

each zone is provided with salt melt as a heat carrier by its own salt pump; the feed of the salt melt is, for example, below the deflecting plate and the withdrawal is, for example, above the deflecting plate;

a substream is, for example, removed from both salt melt circuits and cooled, for example, in one common or two separate indirect heat exchangers (steam generation);

in the first case, the cooled salt melt stream is divided, combined with the particular residual stream and pressurized into the reactor by the particular pump into the appropriate annular channel which divides the salt melt over the circumference of the vessel;

the salt melt reaches the tube bundle through the window disposed in the reactor jacket; the flow is, for example, in a radial direction to the tube bundle;

in each zone, the salt melt flows around the catalyst tubes as dictated by the deflection plate, for example in the sequence
from the outside inward,
from the inside outward;

the salt melt flows through a window mounted around the circumference of the vessel and collects at the end of each zone in an annular channel disposed around the reactor jacket, in order to be pumped in a circuit including substream cooling;

the salt melt is conducted from bottom to top through each reaction zone.

The reaction gas mixture leaves the reactor of the reaction stage according to the invention at a temperature a few degrees higher than the salt bath entrance temperature. For further processing, in a downstream acrolein oxidation stage, the reaction gas mixture is advantageously cooled to from 220° C. to 280° C., preferably from 240° C. to 260° C., in a separate aftercooler which is connected downstream of the reactor of the $1^{st}$ stage.

The aftercooler is generally flanged on below the lower tube plate and normally consists of tubes of ferritic steel. Stainless steel sheet metal spirals which may be partly of fully wound are advantageously introduced into the interior of the tubes of the aftercooler, in order to improve the heat transfer.

Salt Melt:

The salt melt used may be a mixture of 53% by weight of potassium nitrate, 40% by weight of sodium nitrite and 7% by weight of sodium nitrate; both reaction zones and the aftercooler advantageously use a salt melt of the same composition; the amount of salt pumped by circulation in the reaction zones may be approx. 10 000 $m^3$/h per zone.

Flow Control:

The starting reaction gas mixture advantageously flows from top to bottom through the first stage reactor, while the salt melts having different temperatures of the individual zones are advantageously conveyed from bottom to top;

Catalyst tube and thermal tube charge (from top to bottom), for example:

Section 1: length 50 cm steatite rings of geometry 7 mm×7 mm×4 mm (external diameter×length×internal diameter) as a preliminary bed.

Section 2: length 140 cm catalyst charge of a homogeneous mixture of 30% by weight of steatite rings of geometry 5 mm×3 mm×2 mm (external diameter×length×internal diameter) and 70% by weight of unsupported catalyst from section 3.

Section 3: length 160 cm catalyst charge of annular (5 mm×3 mm×2 mm=external diameter×length×internal diameter) unsupported catalyst according to example 1 of DE-A 10046957 (stoichiometry: $[Bi_2W_2O_9 \times 2\ WO_3]_{0.5}$ $[Mo_{12}Co_{5.5}Fe_{2.94}Si_{1.59}K_{0.08}O_x]_1$).

Alternatively, the catalyst tube and thermal tube charge (from top to bottom) can also have the following appearance:

Section 1: length 50 cm steatite rings of geometry 7 mm×7 mm×4 mm (external diameter×length×internal diameter) as a preliminary bed.

Section 2: length 300 cm catalyst charge of annular (5 mm×3 mm×2 mm=external diameter×length×internal diameter) unsupported catalyst according to example 1 of DE-A 10046957 (stoichiometry: $[Bi_2W_2O_9 \times 2WO_3]_{0.5}$. $[Mo_{12}Co_{5.6}Fe_{2.94}Si_{1.59}K_{0.08}O_x]_1$).

In all of the charges mentioned, the unsupported catalyst from example 1 of DE-A 10046957 can also be replaced by:

a) a catalyst according to example 1c of EP-A 15565 or a catalyst to be prepared in accordance with this example, except having the active composition $Mo_{12}Ni_{6.5}Zn_2Fe_2Bi_1P_{0.0065}K_{0.06}O_x \cdot 10\ SiO_2$;

b) example No. 3 of DE-A 19855913 as an unsupported hollow cylinder catalyst of geometry 5 mm×3 mm×2 mm or 5 mm×2 mm×2 mm;

c) unsupported multimetal oxide II catalyst according to example 1 of DE-A 19746210;

d) one of the coated catalysts 1, 2 and 3 of DE-A 10063162, except applied in the same coating thickness to support rings of geometry 5 mm×3 mm×1.5 mm or 7 mm×3 mm×1.5 mm.

According to the invention, the fixed catalyst bed is advantageously otherwise selected in such a way (for example by dilution with, for example, inert material) that the temperature difference between the heating point maximum of the reaction gas mixture in the individual reaction zones and the particular temperature of the reaction zone generally does not exceed 80° C. This temperature difference is usually $\leq 70°$ C., frequently from 20 to 70° C., and this temperature difference is preferably small. For safety reasons, the fixed catalyst bed 1 is also selected in a manner known per se to those skilled in the art (for example by dilution with, for example, inert material) in such a way that the peak-to-salt-temperature sensitivity as defined in EP-A 1106598 is $\leq 9°$ C., or $\leq 7°$ C., or $\leq 5°$ C., or $\leq 3°$ C.

The reactor arrangement described including its charges with fixed bed catalyst can also be operated at high propene loadings, as described in the documents WO 01/36364, DE-A 19927624, DE-A 19948248, DE-A 19948523, DE-A 19948241, DE-A 19910506, DE-A 10302715 and EP-A 1106598.

Preference is given to the reaction zones A and B having the temperatures recommended in this document, except that, in accordance with the teaching of the above-mentioned documents, the second reaction zone in each case has a higher temperature than the first reaction zone in each case. The heating point temperature in the second reaction zone is preferably always below that of the first reaction zone in each case.

However, the propene loadings according to the invention with the procedure according to the invention result in an increased selectivity of acrolein formation relative to the procedure recommended for high propene loadings.

EXAMPLES AND COMPARATIVE EXAMPLES

A reaction tube (V2A steel; external diameter 30 mm, wall thickness 2 mm, internal diameter 26 mm, length: 350 cm, and also a thermal tube (external diameter 4 mm) centered in the middle of the reaction tube to receive a thermal element which can be used to determine the temperature in the reaction tube over its entire length) was charged from top to bottom as follows:

Section 1: length 50 cm steatite rings of geometry 7 mm×7 mm×4 mm (external diameter×length×internal diameter) as a preliminary bed.

Section 2: length 140 cm catalyst charge of a homogeneous mixture of 30% by weight of steatite rings of geometry 5 mm×3 mm×2 mm (external diameter×length×internal diameter) and 70% by weight of unsupported catalyst from section 3.

Section 3: length 160 cm catalyst charge of annular (5 mm×3 mm×2 mm=external diameter×length×internal diameter) unsupported catalyst according to example 1 of DE-A 10046957 (stoichiometry: $[Bi_2W_2O_9 \times 2\ WO_3]_{0.5}$ $[Mo_{12}Co_{5.5}Fe_{2.94}Si_{1.59}K_{0.08}O_x]_1$).

The first 175 cm from top to bottom were thermostatted by means of a salt bath A pumped in countercurrent. The second 175 cm were thermostatted by means of a salt bath B pumped in countercurrent.

The above-described first reaction stage was continuously charged with a starting reaction gas mixture 1 of the following composition, and the loading and the thermostatting of the first reaction tube were varied:

from 6 to 6.5% by volume of propene, from 3 to 3.5% by volume of $H_2O$, from 0.3 to 0.5% by volume of CO, from 0.8 to 1.2% by volume of $CO_2$, from 0.01 to 0.04% by volume of acrolein, from 10.4 to 10.7% by volume of $O_2$ and the remainder ad 100% of molecular nitrogen.

The reaction gas mixture flowed through the reaction tube from top to bottom.

The pressure at the entrance to the reaction tube varied between 2.3 and 3.1 bar as a function of the propene hourly space velocity selected.

A small sample was taken from the product gas mixture at the reaction tube exit for gas chromatography analysis. At the end of reaction zone A, there was likewise an analysis point.

The results achieved as a function of the selected hourly space velocities and the selected salt bath temperatures are shown by the following table (the letter E in brackets means example and the letter C in brackets means comparative example).

$T_A$, $T_B$, are the temperatures of the salt baths circulated by pumping in the reaction zones A and B.

$C_{PA}$ is the propene conversion at the end of reaction zone A in mol %.

$C_{PB}$ is the propene conversion at the end of reaction zone B in mol %.

$S_{AC}$ is the selectivity of acrolein formation in the product gas mixture, based on converted propene, in mol %.

$S_{AA}$ is the selectivity of acrylic acid by-production in the product gas mixture, based on converted propene, in mol %.

$T^{maxA}$, $T^{maxB}$ are the highest temperature of the reaction gas mixture within the reaction zones A and B in ° C.

TABLE

| Propene hourly space velocity (I (STP)/ l·h) | $T_A$ | $T_B$ | $T^{maxA}$ | $T^{maxB}$ | $C_{PA}$ | $C_{PB}$ | $S_{AC}$ | $S_{AA}$ |
|---|---|---|---|---|---|---|---|---|
| 130 (E) | 319 | 319 | 384 | 351 | 66.7 | 95.1 | 92.6 | 5.1 |
| 130 (E) | 327 | 313 | 400 | 330 | 70.3 | 94.8 | 93.9 | 4.4 |
| 130 (C) | 311 | 325 | 361 | 372 | 60.8 | 95.0 | 90.9 | 6.2 |
| 185 (C) | 322 | 336 | 380 | 368 | 64.5 | 94.9 | 90.6 | 7.4 |
| 185 (C) | 310 | 344 | 353 | 383 | 57.2 | 95.2 | 89.2 | 8.1 |

We claim:

1. A process for partially oxidizing propene to acrolein in the gas phase under heterogeneous catalysis by conducting a starting reaction gas mixture comprising propene, molecular oxygen and at least one inert gas, and containing the molecular oxygen and the propene in a molar O2:C3H6 ratio of $\geq 1$, in one reaction stage over a fixed catalyst bed which is arranged in two spatially successive reaction zones A, B, the temperature of reaction zone A being a temperature in the range from 290 to 380° C. and the temperature of reaction zone B likewise being a temperature in the range from 290 to 380° C., and whose active composition is at least one multimetal oxide comprising the elements Mo, Fe and Bi, in such a way that reaction zone A extends up to a conversion of propene of from 40 to 80 mol % and, on single pass of the starting reaction gas mixture through the entire fixed catalyst bed, the propene conversion is $\geq 90$ mol % and the selectivity of acrolein formation, based on converted propene, is $\geq 90$ mol %, the chronological sequence in which the starting reaction gas mixture flows through the reaction zones corresponding to the alphabetic sequence of the reaction zones, wherein
  a) the hourly space velocity of the propene contained in the starting reaction gas mixture on the fixed catalyst bed is <160 l (STP) of propene/l of fixed catalyst bed·h and $\geq 90$ l (STP) of propene/l of fixed catalyst bed·h,
  b) the volume-specific activity of the fixed catalyst bed is either constant or increases at least once in the flow direction of the reaction gas mixture over the fixed catalyst bed, and
  c) the difference $T^{maxA} - T^{maxB}$, formed from the highest temperature $T^{maxA}$ which the reaction gas mixture has within reaction zone A and the highest temperature $T^{maxB}$ which the reaction gas mixture has within reaction zone B, is $\geq 0°$ C.

2. The process as claimed in claim 1, wherein the difference $T^{maxA} - T^{maxB}$ is $\geq 0°$ C. and $\leq 80°$ C.

3. The process as claimed in claim 1, wherein the difference $T^{maxA} - T^{maxB}$ is $\geq 3°$ C. and $\leq 70°$ C.

4. The process as claimed in claim 1, wherein the difference $T^{maxA} - T^{maxB}$ is $\geq 20°$ C. and $\leq 60°$ C.

5. The process as claimed in claim 1, wherein the hourly space velocity of the propene contained in the starting reaction gas mixture on the fixed catalyst bed is $\geq 90$ l (STP) of propene/l·h and $\leq 155$ l (STP) of propene/l·h.

6. The process as claimed in claim 1, wherein the hourly space velocity of the propene contained in the starting reaction gas mixture on the fixed catalyst bed is $\geq 100$ l (STP) of propene/l·h and $\leq 150$ l (STP) of propene/l·h.

7. The process as claimed in claim 1, wherein the active composition of the fixed catalyst bed is at least one multimetal oxide of the general formula I $$Mo_{12}Bi_aFe_bX^1_cX^2_dX^3_eX^4_fO_n \quad (I)$$

wherein the variables are defined as follows:
  $X^1$=nickel and/or cobalt,
  $X^2$=thallium, an alkali metal and/or an alkaline earth metal,
  $X^3$=zinc, phosphorus, arsenic, boron, antimony, tin, cerium, lead and/or tungsten,
  $X^4$=silicon, aluminum, titanium and/or zirconium,
  a=from 0.5 to 5,
  b=from 0.01 to 5,
  c=from 0 to 10,
  d=from 0 to 2,
  e=from 0 to 8,
  f=from 0 to 10 and
  n=a number which is determined by the valency and frequency of the elements other than oxygen in I.

8. The process as claimed in claim 1, wherein the volume-specific activity of the fixed catalyst bed increases at least once.

9. The process as claimed in claim 7, wherein:
  b=from 2 to 4,
  c=from 3 to 10,
  d=from 0.02 to 2, and
  e=from 0 to 5.

10. The process of claim 1, wherein the hourly space velocity of the propene in the starting gas mixture on the fixed catalyst bed is from 90 l (STP) of propene/l of fixed catalyst bed·h to 150 l (STP) of propene/l of fixed catalyst bed·h.

11. The process of claim 1, wherein the temperature of reaction zone A is from 290 to 327° C. and the temperature of reaction zone B is from 290 to 313° C.

12. The process of claim 1, wherein the temperature of reaction zone A is from 319 to 327° C. and the temperature of reaction zone B is from 313 to 319° C.

13. The process of claim 1, wherein the temperature of reaction zone A is from 310 to 340° C.

14. The process of claim 1, wherein the propene conversion in reaction zone A is from 50 to 70 mol %.

15. The process of claim 1, further comprising:
  cooling the reaction gas mixture after the reaction gas mixture has been conducted over the fixed catalyst bed having reaction zones A and B.

16. The process of claim 1, wherein the starting gas mixture comprises from 6 to 15% by volume of propene, from 4 to 20% by volume of water, and from 0 to 10% by volume of constituents other than propene, water, oxygen and nitrogen.

17. The process of claim 1, wherein the starting gas mixture comprises from 7 to 11% by volume of propene, from 6 to 12% by volume of water, and from 0 to 5% by volume of constituents other than propene, water, oxygen and nitrogen.

18. The process of claim 1, wherein the reaction stage is a two-zone tube bundle reactor.

19. The process of claim 1, wherein the starting reaction gas mixture comprises at least one inert gas selected from the group consisting of molecular nitrogen, propane, ethane, methane, pentane, butane, $CO_2$, CO, steam and mixtures thereof.

20. The process of claim 1, further comprising:
  passing the gas mixture through a downstream acrolein oxidation stage after passing the starting reaction gas mixture through the entire fixed catalyst bed.

* * * * *